US006858759B2

(12) United States Patent
Oyevaar et al.

(10) Patent No.: US 6,858,759 B2
(45) Date of Patent: Feb. 22, 2005

(54) PROCESS FOR MANUFACTURE OF BISPHENOLS

(75) Inventors: Martin Herke Oyevaar, SC Goes (NL); Rudy Francois Alain Jos Peemans, Erps-Kwerps (BE); Eduard Hendricus Schlarmann, JP Bergen op Zoom (NL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/639,929

(22) Filed: Aug. 12, 2003

(65) Prior Publication Data

US 2004/0143142 A1 Jul. 22, 2004

Related U.S. Application Data

(63) Continuation-in-part of application No. 10/628,917, filed on Jul. 29, 2003, now abandoned, which is a continuation of application No. 10/248,155, filed on Dec. 20, 2002, now Pat. No. 6,635,788.

(51) Int. Cl.$^7$ .............................................. C07C 39/16
(52) U.S. Cl. ...................... 568/728; 568/727; 528/196
(58) Field of Search ............................... 568/727, 728; 528/196

(56) References Cited

U.S. PATENT DOCUMENTS

| 3,627,846 | A | 12/1971 | Meyer |
| 4,156,098 | A | 5/1979 | Li |
| 4,300,000 | A | 11/1981 | Reinitz |
| 4,308,404 | A | 12/1981 | Kwantes et al. |
| 4,368,315 | A | 1/1983 | Sikdar |
| 4,400,555 | A | 8/1983 | Mendiratta |
| 4,590,303 | A | 5/1986 | Mendiratta |
| 4,918,245 | A | 4/1990 | Iimuro et al. |
| 5,210,329 | A | 5/1993 | Gomes de Matos et al. |
| 5,288,837 | A | 2/1994 | Munjal et al. |
| 5,300,700 | A | 4/1994 | Malamet et al. |
| 5,315,042 | A | 5/1994 | Cipullo et al. |
| 5,723,689 | A | 3/1998 | Pressman et al. |
| 5,783,733 | A | 7/1998 | Kissinger |
| 5,786,522 | A | 7/1998 | Cipullo |
| 5,990,362 | A | 11/1999 | Pressman et al. |
| 6,133,486 | A | 10/2000 | Maas et al. |
| 6,197,916 | B1 | 3/2001 | Pressman et al. |
| 6,635,788 | B1 | * 10/2003 | Oyevaar et al. ............ 568/728 |

FOREIGN PATENT DOCUMENTS

| DE | 2 315 888 | 10/1974 |
| EP | 0 559 372 | 2/1993 |
| EP | 0 812 815 | 6/1997 |

OTHER PUBLICATIONS

"Kirk–Othmer Encyclopedia of Chemical Technology," 4$^{th}$ Ed., vol. 19, pp. 584–599 (1996).*
Encyclopedia of Chemical Technology: Fourth Edition, New York, John Wiley and Sons. vol. 14, pp. 777–778 (1995).
Encyclopedia of Chemical Technology: Third Edition, New York, John Wiley and Sons. vol. 9, pp. 256, 296–297 (1980).
Encyclopedia of Chemical Technology: Third Edition. New York, John Wiley and Sons. vol. 13, pp. 678–696 (1981).
Encyclopedia of Chemical Technology: Third Edition, New York, John Wiley and Sons. vol. 13, pp. 701–705 (1981).
International Search Report dated May 17, 2004.

* cited by examiner

*Primary Examiner*—Michael L. Shippen

(57) ABSTRACT

A method for the manufacture of bisphenols comprises introducing a combined feed stream comprising a feed stream and a recycle stream into a reactor system comprising at least one reactor containing a catalytic proportion of an acid catalyst and wherein the combined feed stream comprises a carbonyl compound and a stoichiometric excess of phenol; removing from the reactor system a reactor effluent; splitting the reactor effluent into a crystallization feed stream and an effluent recycle stream; extracting from said crystallization feed stream a bisphenol adduct, remainder comprising a mother liquor stream; dehydrating said mother liquor stream and said effluent recycle stream in a dehydrator wherein excess water and carbonyl compound are removed; and recycling the dehydrated mother liquor and the dehydrated effluent recycle stream back to the combined feed stream to effect improved production of p,p-bisphenol, along with increased reactor selectivity and reduced promoter quantities.

26 Claims, 1 Drawing Sheet

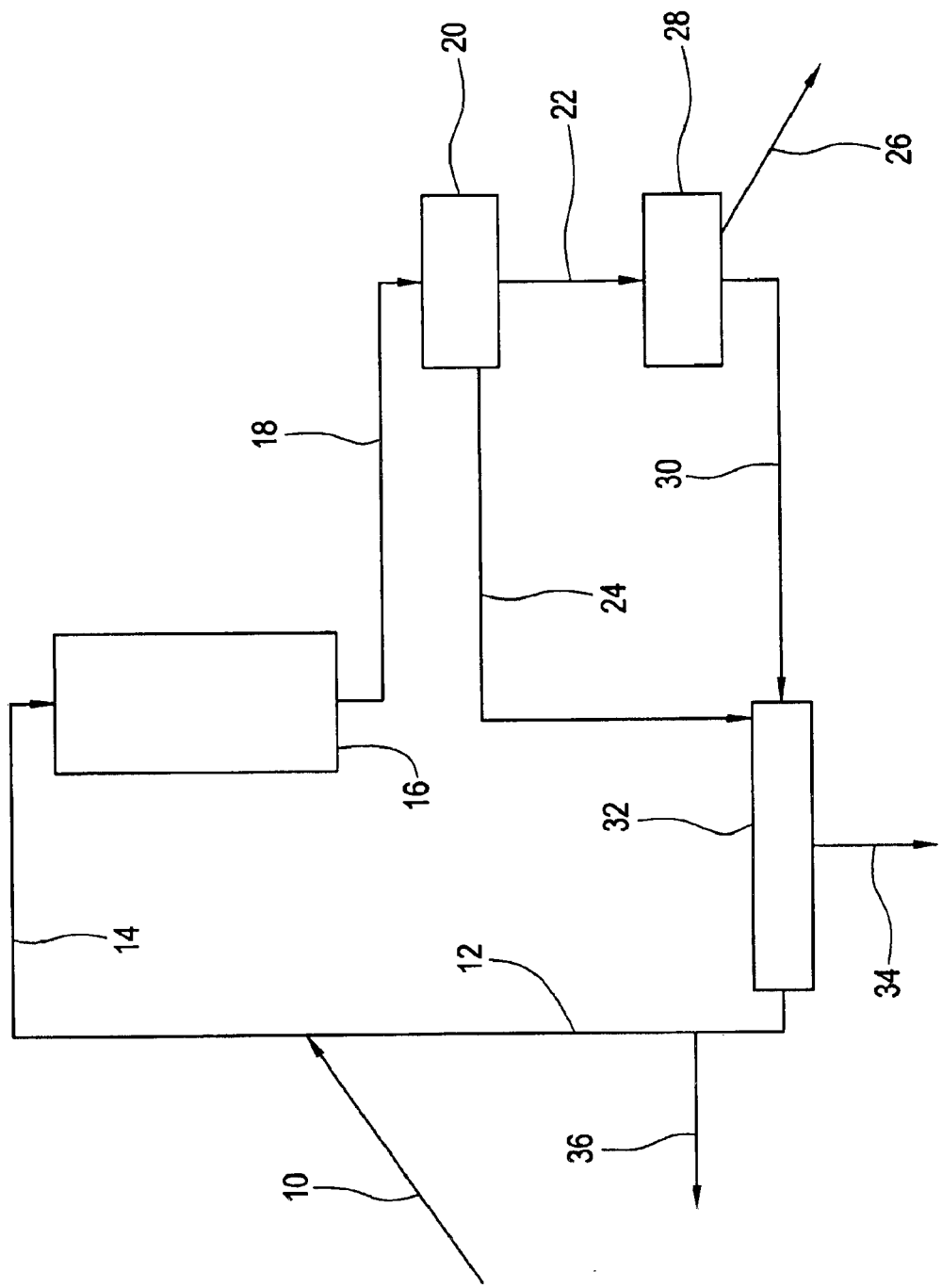

PROCESS FOR MANUFACTURE OF BISPHENOLS

CROSS REFERENCE TO RELATED APPLICATIONS

This application is a Continuation-in-Part of U.S. application Ser. No. 10/628,917 filed on Jul. 29, 2003 now abandoned, which is a Continuation of U.S. application Ser. No. 10/248,155 filed on Dec. 20, 2002 now U.S. Pat. No. 6,635,788, the entire contents of which are herein incorporated by reference.

BACKGROUND

The present disclosure relates to methods for the manufacture of bisphenols. In particular, the present disclosure relates to methods for improving the efficiency of the manufacture of bisphenols.

Bisphenols are used as raw materials in the preparation of chemical products such as epoxy resins and polycarbonates. They are commonly prepared by the condensation of phenols and ketones in the presence of either an acid catalyst, or an active ion exchange catalyst. Often, a promotor (often referred to as a co-catalyst) is used in the reaction.

Typically the catalysts used in the production of bisphenols undergo rapid deactivation. There are many possible reasons for deactivation, including the presence of excess acetone, bisphenolic tars, and other reaction by-products. Replacing the catalyst is expensive, requires significant labor under adverse conditions, and creates chemical wastes that must be properly disposed of. The use of a promotor while advantageous to the reaction is extremely expensive and any reduction in promotor quantity while maintaining or increasing reactor output is highly desirable.

A particular route for improved bisphenol production and increased catalyst lifetimes involves recycling effluent from the reactor. For example, U.S. Pat. No. 4,308,404 teaches that recycling effluent from any one reactor, which is part of a series, back to the reaction zone, can increase catalyst life. This patent requires however that the reaction zone be constituted of at least two reactors in order to increase catalyst life. Further, it proscribes recycling effluent from the last reactor to the reaction zone.

U.S. Pat. No. 5,786,522 also teaches partial recycling of dehydrated effluent from the reactor back into the input stream in order to produce bisphenols, which are further utilized in polycarbonates to improve color.

Despite a large number of methods proposed for the production of bisphenols, there nonetheless remains a need in the art for effective, efficient methods that are suitable for large-scale, industrial production processes.

BRIEF DESCRIPTION OF THE DRAWINGS

The FIGURE is a process flow diagram showing an embodiment of a method for improved bisphenol production, increased catalyst lifetimes, improved reactor selectivity and reduced promotor quantity.

SUMMARY

A method for the manufacture of bisphenols comprises introducing a combined feed stream comprising a feed stream and a recycle stream into a reactor system comprising at least one reactor containing a catalytic proportion of an acid catalyst and wherein the combined feed stream comprises a carbonyl compound and a stoichiometric excess of phenol; removing from the reactor system a reactor effluent; splitting the reactor effluent into a crystallization feed stream and an effluent recycle stream; extracting from said crystallization feed stream a bisphenol adduct, remainder comprising a mother liquor stream; dehydrating said mother liquor stream and said effluent recycle stream in a dehydrator stream wherein excess water and carbonyl compound are removed; and recycling the dehydrated mother liquor and the dehydrated effluent recycle stream back to the combined feed stream to effect improved production of p,p-bisphenol, along with increased reactor selectivity and reduced promoter quantities.

DETAILED DESCRIPTION OF PREFERRED EMBODIMENTS

The inventors hereof have discovered that in the process for manufacturing p,p-bisphenol (hereinafter BPA), reduction in carbonyl compound concentrations in the combined feed stream 14 can be used to improve reactor selectivity. The reduction in carbonyl compound concentrations in the combined feed stream 14 is achieved by dehydrating a portion of the reactor effluent 18 such that there occurs an increase in the phenol/BPA concentrations with a consequent improved catalyst performance and increased reactor selectivity. During the dehydrating of the reactor effluent 18, the reduction in the carbonyl compound content along with the water content results in a corresponding increase in the phenol/BPA concentration in the recycle stream 12 emanating from the dehydrator which consequently leads to an increase in the phenol/BPA content in the combined feed stream 14.

Alternatively if the carbonyl compound is returned to its original value by the re-addition of fresh carbonyl compound to the combined feed stream 14, plant capacity for the production of p,p-bisphenol is tremendously increased, or the promoter usage can be reduced.

In an advantageous mode of operation, it is desirable to recycle an amount greater than or equal to about 6, preferably greater than or equal to about 8, more preferably greater than or equal to about 10 wt % of the reactor effluent 18 to the combined feed stream 14. It is also desirable to recycle an amount of less than or equal to about 22, preferably less than or equal to about 20, more preferably less than or equal to about 18 wt % of the reactor effluent 18. In recycling the reactor effluent 18 between the above-specified amounts, the carbonyl compound concentration in the combined feed stream 14 can be reduced by an amount greater than or equal to about 15, preferably greater than or equal to about 20, more preferably greater than or equal to about 25 wt % when compared with a process where the reactor effluent 18 is not recycled. Similarly the carbonyl compound in the feed stream can be reduced by an amount less than or equal to about 35, preferably less than or equal to about 30, more preferably less than or equal to about 28 wt % of the combined feed stream 14. In addition, promotor concentration is reduced by an amount greater than or equal to about 10, preferably greater than or equal to about 15, more preferably greater than or equal to about 20 wt % as compared with a process wherein the reactor effluent 18 is not recycled. In general, the promotor concentration can be reduced by an amount of less than or equal to about 30, preferably less than or equal to about 28, more preferably less than or equal to about 25 wt % as compared with a process wherein the reactor effluent 18 is not recycled, while maintaining constant production output. Further, in a special embodiment involving increased production, without any reduction in carbonyl compound and promotor concentration, an increase in the daily production rate of BPA of greater than or equal to about 5, preferably greater than or equal to about 6, more preferably greater than or equal to about 7 wt % can be achieved through recycling a portion of the reactor effluent 18. Similarly daily production rate of BPA can be increased by an amount of less than or equal to about 11, preferably less than or equal to about 10, most preferably less than or equal to about 8.5 wt % can be achieved through recycling a portion of the reactor effluent 18.

In general, phenols suitable for use in preparing the bisphenols have a reactive hydrogen preferably in the para-position relative to the phenolic hydroxyl groups. Such phenols may be substituted by one or more alkyl groups such as lower alkyl groups, e.g., methyl, ethyl or tertiary butyl groups, halogen atoms such as chlorine atoms, other substituents which do not interfere with the carbonyl condensation reaction, or combinations comprising at least one of the following phenols. Exemplary phenols include ortho- and meta-cresol, 2,6-dimethylphenol ortho-sec.butylphenol, 1,3,5 xylenol, tetramethylphenol, 2-methyl-6-tert.butylphenol, orthophenylphenol, ortho- and meta-chlorophenol, ortho-bromophenol, 2,6-dichlorophenol, and the like. Most preferred is phenol.

The carbonyl compounds used in the process may be aldehydes, or ketones. Preferably, the carbonyl compounds are ketones. Specific ketones include acetone, methyl ethyl ketone, methyl propylketone, methyl vinyl acetone, acetophenone and cyclohexanone, and combinations compromising at least one of the foregoing ketones. Particularly preferred is acetone.

A variety of catalyst systems may be used in the process as desired. Homogeneous catalysts like hydrochloric acid, sulfuric acid, or Lewis acids would be suitable for some embodiments. However, heterogeneous catalyst systems are preferred. In particular, the use of an ion exchange resin is often the most efficient means of catalysis. These resins participate in fewer side reactions. Moreover, because they are insoluble, they remain in the reactor system, and do not contribute to downstream corrosion problems.

Ion-exchange resins are well known in the art and described in various sources, such as Kirk-Othmer's Encyclopedia of Chemical Technology, 3rd Edition, Vol. 9, pp. 256 and 296–297 (1980); and Vol. 13, pp. 678 et seq. (1981). The use of ion-exchange resins for catalysis is also described in Kirk-Othmer's Encyclopedia of Chemical Technology, 4th Edition, Vol. 14, pp. 777–778 (1995). In particular, strong-acid types of resins are suitably employed. Preferably, the catalysts are sulfonated aromatic resins comprising hydrocarbon polymers having a plurality of pendant sulfonic acid groups. The pendant sulfonic acid groups are typically 2 or 4% divinyl benzene crosslinked. Sulfonated polystyrene, poly(styrenedivinylbenzene) copolymer, and sulfonated phenolformaldehyde resins have utility in this regard. Commercial examples of suitable ion exchange resins are the AMBERLYST® materials (e.g., AMBERLYST® 15) and AMBERLITE® materials (e.g., AMBERLITE® 131 and AMBERLITE® 118), available from Rohm & Haas Company; and the DOWEX® products, which are available from Dow Chemical Company, as well as K1131 and K1221 from Bayer Chemical Company.

The exchange capacity of the acidic resin is preferably at least about 2.0 milliequivalents (meq of hydrogen ion ($H^+$) per gram of dry resin. Ranges in an amount of about 3.0 to about 5.5 meq $H^+$ per gram of dry resin are most preferred.

In prior art processes for preparing various bisphenols, the ion exchange resin catalysts often required pre-treatment with a sulfur-comprising promoter. Examples include thiol i.e. (mercaptan)-based compounds such as methyl mercaptan, ethyl mercaptan, propyl mercaptan, 3-mercaptopropionic acid (hereinafter referred to as 3-mpa) or combinations comprising at least one of the aforementioned promoters, which are covalently or ionically linked/bonded to the catalyst. Preferably, the promotor is 3-mpa. A reduction in the amount of promotor can represent considerable savings especially in a large scale manufacturing operation.

It is generally desirable for the promotor to be present in an amount of greater than or equal to about 500, preferably greater than or equal to about 750, more preferably greater than or equal to about 1000 ppm with respect to the total weight of the combined feed stream. It is also generally desirable for the promotor to be present in an amount of less than or equal to about 10,000, preferably less than or equal to about 5000, more preferably less than or equal to about 4500 ppm with respect to the total weight of the combined feed stream.

Referring now to the FIGURE, a process flow diagram schematically depicts an exemplary embodiment for manufacture of bisphenols. A feed stream 10 comprising a carbonyl compound and phenol, as described above, is combined with a recycle stream 12 forming a combined feed 14 that is introduced into a reactor 16. In one embodiment, reactor 16 is generally a catalyst reactor comprising divinyl benzene cross-linked sulfonated polystyrene ion exchange resin catalyst in the form of large beds within tanks and optionally includes one or more promoters described above.

Reactor effluent 18, emanating from the reactor, is distributed by splitter 20 into an effluent recycle stream 24 and a crystallization feed stream 22. A bisphenol adduct 26 (which may contain other components such as phenol) is derived from crystallization feed stream 22 via a crystallization step 28, such as a multiple-stage crystallization and/or distillation. In certain embodiments, the effluent at the crystallizer is distilled generally to remove excess phenol, and the distillate is then crystallized to obtain BPA crystalline adduct. A mother liquor stream 30 obtained after the removal of the bisphenol adduct along with effluent recycle stream 24, are dehydrated at a dehydrator 32. The excess water and/or acetone is removed via an excess stream 34, resulting in recycle stream 12. A purge stream 36 is further removed.

In one embodiment, the combined feed stream 14, which comprises the feed stream 10 and the recycle stream 12 comprises an amount greater than or equal to about 1, preferably greater than or equal to about 2, most preferably greater than or equal to about 3 wt % carbonyl compound. It is generally desirable for the combined feed stream 14 to have an amount less than or equal to about 8, preferably less than or equal to about 6 and more preferably less than or equal to about 5 wt % carbonyl compound.

The combined feed stream 14 also comprises an amount greater than or equal to about 60, preferably greater than or equal to about 65, most preferably greater than or equal to about 70 wt % phenol based upon the total weight of the combined feed stream 14. It is also generally desirable for the combined feed stream 14 to comprise an amount of less than or equal to about 85, preferably less than or equal to about 80, more preferably less than or equal to about 78 wt % phenol based on the total weight of the combined feed stream 14. Additionally, the combined feed stream 14 may comprise about 0.01 to about 3 wt % water, about 5 to about 20 wt % p,p-bisphenol and about 1 to about 7 wt % o,p-bisphenol. All the aforementioned weight percentages are with respect to the total weight of the combined feed stream 14.

The reactor effluent 18 emanating from reactor 16 generally comprises the following constituents, weight percentages being measured with respect to the total weight of constituents in the reactor effluent 18. It comprises greater than or equal to about 0.1, preferably greater than or equal to about 0.2, most preferably greater than or equal to about 0.3 wt % carbonyl compound. In general, the reactor effluent 18 emanating from reactor 16 comprises less than or equal to about 1.8, preferably less than or equal to about 1.2 and more preferably less than or equal to about 0.75 wt % carbonyl compound. The reactor effluent 18 also comprises greater than or equal to about 50, preferably greater than or equal to about 55, most preferably greater than or equal to about 60 wt % phenol. The reactor effluent 18 must also comprise an amount of less than or equal to about 75, preferably less than or equal to about 70, more preferably less than or equal to about 65 wt % phenol. The p,p-bisphenol which is the chief objective of the process is present in the reactor effluent 18 in an amount of greater than or equal to about 20, preferably greater than or equal to 21, more preferably greater than or equal to about 22 wt % of the reactor effluent 18. In general the p,p-bisphenol is present in the reactor effluent 18 in an amount of less than or equal to about 30, preferably less than or equal to about 28 wt % and more preferably less than or equal to about 26 wt % of the reactor effluent. In addition water which is a byproduct of the condensation reaction between the carbonyl compound and phenol is present at about 0.5 to 3 wt %, along with o,p-bisphenol at about 1 to about 7 wt % and a small amount of other reactants introduced into reactor 16 as part of the combined feed stream 10.

The reactor effluent 18 is subsequently directed to a splitter where an amount greater than or equal to about 3, preferably greater than or equal to about 5, more preferably greater than or equal to about 8 wt % of total effluent is split off into a effluent recycle stream 24 and sent to the dehydrator 32. It is also generally desirable to split off from the reactor effluent 18 an amount less than or equal to about 30, preferably less than or equal to about 28, more preferably less than or equal to about 25 wt % of reactor effluent 18 to effluent recycle stream 24. Optionally, if a portion of the reactor effluent 18 is recycled, the flow over the reactor has to be increased in order to maintain an undiminished supply of effluent to the crystallizer. After the bisphenol/phenol adduct is crystallized out, the remainder called the mother liquor 30 is sent to the dehydrator where it is combined with the effluent recycle stream 24 to be stripped of water and optionally acetone.

In one embodiment the dehydrated recycle stream 12 emanating from the dehydrator comprises about 70 to about 80 wt % phenol, about 0.1 to about 0.3 wt % water, about 0.1 to about 1 wt % carbonyl compound, about 8 to about 15 wt % p,p-bisphenol, about 3 to about 4 wt % o,p-bisphenol, about 0.5 to about 1.5 wt % chromane, about 1 to 1.5 wt % dimers and about 0.7 to about 1.5 wt % of BPX-1.

In a preferred embodiment, in one manner of proceeding, the reactor is first started up by feeding a mixture of carbonyl compound and phenol in the form of feed stream 10 to the reactor. The carbonyl compound and the phenol undergo a reaction in the reactor 16 to yield the reactor effluent 18 which eventually yields the combined feed stream 14 following the removal of the bisphenol adduct and the dehydration of water and acetone as described above.

Following the start-up of the reactor, in successive processes or cycles to yield bisphenol, the feed stream 10 is combined with the dehydrated recycle stream 12 to form the combined feed stream 14. The temperature of the combined feed stream 14 is generally adjusted as desired. After hydraulic flow of the combined feed stream 14 over the cationic exchange resin in the reactor 16, effluent containing bisphenol product is removed from the reactor and directed to the splitter 20, wherein a certain portion of the effluent is further directed to the crystallizer 26 where bisphenol is crystallized out. The mother liquor 30 together with the effluent recycle stream 24 is sent to the dehydrator either simultaneously or sequentially. After removal of water and acetone through dehydration and purging, the dehydrated recycle stream 12 is combined with fresh phenol and acetone to reconstitute the combined feed stream 14. Bisphenol production is generally increased as a result of recycling effluent.

In one embodiment, the bisphenols obtained by recycling effluent may be used to manufacture polycarbonates. As used herein, the terms "polycarbonate", "polycarbonate composition", and "composition comprising aromatic carbonate chain units" includes compositions having structural units of the formula (I):

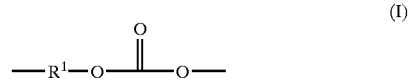
(I)

in which greater than or equal to about 60 percent of the total number of $R^1$ groups are aromatic organic radicals and the balance thereof are aliphatic, alicyclic, or aromatic radicals. Preferably, $R^1$ is an aromatic organic radical and, more preferably, a radical of the formula (II):

(II)

wherein each of $A^1$ and $A^2$ is a monocyclic divalent aryl radical and $Y^1$ is a bridging radical having zero, one, or two atoms which separate $A^1$ from $A^2$. In an exemplary embodiment, one atom separates $A^1$ from $A^2$. Illustrative examples of radicals of this type are —O—, —S—, —S(O)—, —S(O$_2$)—, —C(O)—, methylene, cyclohexylmethylene, 2-[2,2,1]-bicycloheptylidene, ethylidene, isopropylidene, neopentylidene, cyclohexylidene, cyclopentadecylidene, cyclododecylidene, adamantylidene, or the like. In another embodiment, zero atoms separate $A^1$ from $A^2$, with an illustrative example being bisphenol. The bridging radical $Y^1$ can be a hydrocarbon group or a saturated hydrocarbon group such as methylene, cyclohexylidene or isopropylidene.

Polycarbonates may be produced by the Schotten-Bauman interfacial reaction of the carbonate precursor with dihydroxy compounds. Typically, an aqueous base such as sodium hydroxide, potassium hydroxide, calcium hydroxide, or the like, is mixed with an organic, water immiscible solvent such as benzene, toluene, carbon disulfide, or dichloromethane, which contains the dihydroxy compound. A phase transfer agent is generally used to facilitate the reaction. Molecular weight regulators may be added either singly or in admixture to the reactant mixture. Branching agents, described forthwith may also be added singly or in admixture.

Polycarbonates can be produced by the interfacial reaction of dihydroxy compounds in which only one atom separates $A^1$ and $A^2$. As used herein, the term "dihydroxy compound" includes, for example, bisphenol compounds obtained by effluent recycling and having general formula (III) as follows:

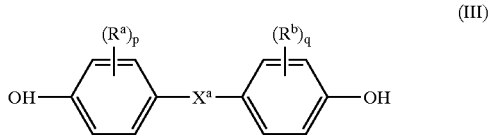

(III)

wherein $R^a$ and $R^b$ each independently represent hydrogen, a halogen atom, or a monovalent hydrocarbon group; p and q are each independently integers from 0 to 4; and $X^a$ represents one of the groups of formula (IV):

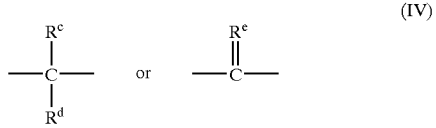

(IV)

wherein $R^c$ and $R^d$ each independently represent a hydrogen atom or a monovalent linear or cyclic hydrocarbon group, and $R^e$ is a divalent hydrocarbon group.

Examples of the types of bisphenol compounds that may be represented by formula (III) include the bis(hydroxyaryl) alkane series such as, 1,1-bis(4-hydroxyphenyl)methane, 1,1-bis(4-hydroxyphenyl)ethane, 2,2-bis(4-hydroxyphenyl)propane (or p,p-bisphenol), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, bis(4-hydroxyphenyl)phenylmethane, 2,2-bis(4-hydroxy-1-methylphenyl)propane, 1,1-bis(4-hydroxy-t-butylphenyl)propane, 2,2-bis(4-hydroxy-3-bromophenyl)propane, or the like; bis(hydroxyaryl)cycloalkane series such as, 1,1-bis(4-hydroxyphenyl)cyclopentane, 1,1-bis(4-hydroxyphenyl)cyclohexane, or the like, or combinations comprising at least one of the foregoing bisphenol compounds.

Other bisphenol compounds that may be represented by formula (III) include those where X is —O—, —S—, —SO— or —SO$_2$—. Some examples of such bisphenol compounds are bis(hydroxyaryl)ethers such as 4,4'-dihydroxy diphenylether, 4,4'-dihydroxy-3,3'-dimethylphenyl ether, or the like; bis(hydroxy diaryl) sulfides, such as 4,4'-dihydroxy diphenyl sulfide, 4,4'-dihydroxy-3,3'-dimethyl diphenyl sulfide, or the like; bis (hydroxy diaryl) sulfoxides, such as, 4,4'-dihydroxy diphenyl sulfoxides, 4,4'-dihydroxy-3,3'-dimethyl diphenyl sulfoxides, or the like; bis(hydroxy diaryl)sulfones, such as 4,4'-dihydroxy diphenyl sulfone, 4,4'-dihydroxy-3,3'-dimethyl diphenyl sulfone, or the like; or combinations comprising at least one of the foregoing bisphenol compounds.

Typical carbonate precursors include the carbonyl halides, for example carbonyl chloride (phosgene), and carbonyl bromide; the bis-haloformates, for example the bis-haloformates of dihydric phenols such as bisphenol A, hydroquinone, or the like, and the bis-haloformates of glycols such as ethylene glycol and neopentyl glycol; and the diaryl carbonates, such as diphenyl carbonate, di(tolyl) carbonate, and di(naphthyl) carbonate. The preferred carbonate precursor for the interfacial reaction is carbonyl chloride.

In one embodiment, the polycarbonate may be produced by a melt polycondensation reaction between a dihydroxy compound and a carbonic acid diester. Examples of the carbonic acid diesters that may be utilized to produce the polycarbonates are diphenyl carbonate, bis(2,4-dichlorophenyl)carbonate, bis(2,4,6-trichlorophenyl) carbonate, bis(2-cyanophenyl) carbonate, bis(o-nitrophenyl) carbonate, ditolyl carbonate, m-cresyl carbonate, dinaphthyl carbonate, bis(diphenyl) carbonate, diethyl carbonate, dimethyl carbonate, dibutyl carbonate, dicyclohexyl carbonate, or the like, or combinations comprising at least one of the foregoing carbonic acid diesters. The preferred carbonic acid diester is diphenyl carbonate.

Preferably, the number average molecular weight of the polycarbonate is about 3,000 to about 1,000,000 grams/mole (g/mole). Within this range, it is desirable to have a number average molecular weight of greater than or equal to about 10,000, preferably greater than or equal to about 20,000, and more preferably greater than or equal to about 25,000 g/mole. Also desirable is a number average molecular weight of less than or equal to about 100,000, preferably less than or equal to about 75,000, more preferably less than or equal to about 50,000, and most preferably less than or equal to about 35,000 g/mole.

The invention is further illustrated by the following non-limiting examples.

EXAMPLE 1

In this simulated baseline example shown in table 1 below, the reactor effluent 18 was not split and all of the effluent was sent to the crystallizer wherefrom the mother liquor was sent to the dehydrator. Bisphenol production processes were established utilizing four reactors each loaded with 35 tons 4% CL catalyst, which is an acidic form of sulfonated polystyrene cross-linked with divinylbenzene having an activity of 1.0 and capable of handling a total hydraulic flow of 150 (cubic meters/hour) m$^3$/hour. Promotor 3-mpa was utilized at 2568 parts per million (ppm). The reactor effluent 18 directed towards the crystallizer was 117 tons/hour. The reaction inlet temperature was maintained at about 56° C. The total bisphenol output/day is shown in the Table 1 below to be 398.95 tons.

TABLE 1

| Process condition/Component | Combined Feed (%) | Effluent (%) |
|---|---|---|
| Total flow over reactors (tons/hr) | 117 | |
| Flow over 1 reactor (tons/hr) | 29.25 | |
| Flow to Crystallizer (tons/hr) | 117 | |
| % recycle of reactor effluent 18 to dehydrator | 0 | |
| Phenol | 74.9 | 63.2 |
| Water | 0.2 | 1.34 |
| Acetone | 4.5 | 0.813 |
| p,p-bisphenol | 11.0 | 24.82 |
| o,p-bisphenol | 3.3 | 3.38 |
| Chromane | 0.8 | 0.83 |
| Dimers | 1.2 | 1.26 |
| BPX-1 | 1.1 | 1.11 |
| Heavies | 2.7 | 2.91 |
| Acetone Load (kg/hr) | | 970 |
| Tons bisphenol/day | | 398.95 |

EXAMPLE 2

Bisphenol production processes were established utilizing four reactors each loaded with 35 tons 4% CL catalyst with activity 1.0 and capable of handling a total hydraulic flow of 150 m$^3$/hour. Reactor inlet temperature was 56° C. Promotor 3-mpa was utilized at 2568 ppm. This case assumes that 10 (and 16)% of the effluent is recycled back to the dehydrator and that the flow over the reactors is increased to maintain the feed to the crystallizer at 117 tons/hr. The fresh acetone/phenol to the process are increased to maintain the same acetone concentration as at present. Inlet temperature is maintained at 56° C. With 10 (or 16)% recycle of reactor effluent 18 to dehydration, the following equilibrium shown in Table 2 is reached. It can also be seen that if acetone concentrations are maintained at a constant levels relative to the total weight of all inputs that the bisphenol production is increased dramatically (426.3 tons/day at 10% recycle) when compared with the production in example 1 (398.95 tons/day) wherein no recycle was attempted.

TABLE 2

| Process condition/ Component | 10% recycle | | 16% recycle | |
|---|---|---|---|---|
| | Combined feed (%) | Effluent (%) | Combined feed (%) | Effluent (%) |
| Total flow over reactors (tons/hour) | 130 | | 139.2 | |
| Flow over 1 reactor (tons/hour) | 32.5 | | 34.8 | |
| Flow to crystallizer (tons/hour) | 117 | | 117 | |
| % recycle of reactor effluent 18 to dehydrator | | 10 | | 16 |
| phenol | 73.5 | 62.2 | 72.3 | 61.4 |
| water | 0.2 | 1.30 | 0.204 | 1.28 |
| acetone | 4.5 | 0.94 | 4.52 | 1.05 |
| p,p-bisphenol | 12.41 | 25.58 | 13.4 | 26.22 |
| o,p-bisphenol | 3.3 | 3.45 | 3.33 | 3.52 |
| chromane | 0.8 | 0.83 | 0.8 | 0.83 |
| dimers | 1.2 | 1.26 | 1.21 | 1.27 |
| BPX-1 | 1.1 | 1.15 | 1.11 | 1.17 |
| heavies | 2.7 | 2.94 | 2.75 | 2.99 |
| Acetone Load (kg/hr) | | 1222 | | 1459 |
| Tons BPA/day | | 426.3 | | 444 |

EXAMPLE 3

Bisphenol production processes were established utilizing four reactors each loaded with 35 tons 4% crosslinked (CL) catalyst with activity 1.0 and capable of handling a total hydraulic flow of 150 m³/hour. Reactor inlet temperature was 56° C. This case assumes that 10% of the reactor effluent 18 is recycled back to the process reactor feed via dehydration and that the flow over the reactors is increased to keep the feed to the crystallizer constant at 117 tons/hr. The fresh acetone and phenol feed to the process is increased slightly and the 3-mercapto propionic acid is reduced to maintain the same production as at present. With 10% recycle of reactor effluent 18 to dehydration/reactor feed, and 1928.2 ppm 3-mpa to the reaction feed, the following equilibrium is reached:

TABLE 3

| Process condition/ Component | 10% recycle | |
|---|---|---|
| | Combined feed (%) | Effluent (%) |
| Total flow over reactors (tons/hr) | 130 | |
| Flow over 1 reactor (tons/hr) | 32.5 | |
| Flow to crystallizer (tons/hr) | 117 | |
| % recycle of reactor effluent 18 to dehydrator | | 10 |
| Phenol | 73.8 | 63.3 |

TABLE 3-continued

| Process condition/ Component | 10% recycle | |
|---|---|---|
| | Combined feed (%) | Effluent (%) |
| Water | 0.2 | 1.23 |
| Acetone | 4.23 | 0.925 |
| p,p-bisphenol | 12.4 | 24.82 |
| o,p-bisphenol | 3.31 | 3.36 |
| Chromane | 0.8 | 0.83 |
| Dimers | 1.2 | 1.25 |
| BPX-1 | 1.1 | 1.14 |
| Heavies | 2.72 | 2.92 |
| Acetone Load (kg/hr) | | 1202 |
| Tons BPA/day | | 397.5 |

Thus by comparing the bisphenol output from Example 3 with that of Example 1 it can be seen that by recycling some of the reactor effluent 18, it is possible to use much reduced quantities of the promotor 3-mpa (2568 vs. 1928 ppm) while producing essentially the same output of bisphenol.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method for the manufacture of bisphenols comprising:
   introducing a combined feed stream comprising a feed stream and a recycle stream into a reactor system comprising at least one reactor containing a catalytic proportion of an acid catalyst and wherein the combined feed stream comprises a carbonyl compound and an amount of greater than or equal to about 60 wt % phenol, wherein the weight percents are based on the total weight of the combined feed stream;
   removing from the reactor system a reactor effluent;
   splitting the reactor effluent into a crystallization feed stream and an effluent recycle stream;
   extracting from said crystallization feed stream a bisphenol adduct, remainder comprising a mother liquor stream;
   dehydrating said mother liquor stream and said effluent recycle stream in a dehydrator wherein excess water and carbonyl compound are removed; and
   recycling the dehydrated mother liquor and the dehydrated effluent recycle stream back to the combined feed stream to effect improved production of p,p-bisphenol, along with increased reactor selectivity and reduced promoter quantities.

2. The method of claim 1, wherein the phenol is an ortho-cresol, meta-cresol, 2,6-dimethylphenol, ortho-sec-butylphenol, 1,3,5 xylenol, tetramethylphenol, 2-methyl-6-tert.butylphenol, orthophenylphenol, ortho- and meta-chlorophenol, ortho-bromophenol, 2,6-dichlorophenol, or a combination comprising at least one of the foregoing phenols.

3. The method of claim 1, wherein the carbonyl compound is acetone, methyl ethyl ketone, methyl propylketone, methyl vinyl acetate, acetophenone and cyclohexanone, or a combination comprising at least one of the foregoing ketones.

4. The method of claim 1, wherein the carbonyl compound is acetone.

5. The method of claim 1, wherein the effluent recycle stream comprises about 6 to about 22 wt % of reactor effluent.

6. The method of claim 1, wherein effluent recycle stream comprises about 8 to about 20 wt % of reactor effluent.

7. The method of claim 1, wherein carbonyl compound concentration in the combined feed stream is about 1 to about 8 wt % of the total weight of the combined fee stream.

8. The method of claim 1, wherein p,p-bisphenol concentration in the combined feed stream is about 5 to about 20 wt % of the total weight of the combined feed stream.

9. The method of claim 1, wherein the catalyst is a sulfonated polystyrene, poly(styrenedivinylbenzene) copolymers, sulfonated phenolformaldehyde resins, or a combination comprising at least one of the foregoing catalysts.

10. The method of claim 1, wherein the catalyst is an acidic form of sulfonated polystyrene cross-linked with divinylbenzene having an activity of 1.0 and capable of handling a total hydraulic flow of 150 m$^3$/hour.

11. The method of claim 1 wherein the catalyst comprises pendant sulfonic acid groups having about 2 to about 4% crosslinking of a divinylbenzene.

12. The method of claim 1, wherein the promotor is a methyl mercaptan, ethyl mercaptan, propyl mercaptan, 3-mercaptopropionic acid, or a combination comprising at least one of the foregoing promotors.

13. The method of claim 1, wherein the promotor is 3-mercapto propionic acid and is present in an amount of about 500 to about 10,000 ppm with respect to the total weight of the combined feed stream.

14. A process for the preparation of bisphenols comprising:

reacting acetone with an excess of phenol in a reactor containing a catalyst bed comprising an acidic form of sulfonated polystyrene cross-linked with divinylbenzene having an activity of 1.0, treated with 3-methyl propionic promotor;

splitting the reactor effluent into a crystallization feed stream and an effluent recycle stream, wherein the effluent recycle stream comprises about 6 to about 22 wt % of the reactor effluent;

extracting from the crystallization feed stream a bisphenol adduct to leave behind a mother liquor;

dehydrating the mother liquor and the effluent recycle stream to produce a recycle stream;

combining the recycle stream with a new feed stream to produce a combined feed stream wherein the combination of the recycle stream and feed stream results in an improved production of p,p-bisphenol or reduced levels of promotor.

15. A method of claim 14, wherein the reactor inlet temperature is about 45° C. to about 60° C.

16. A method of claim 14, wherein the p,p-bisphenol concentration in the combined feed stream is about 5 to about 20 wt % of the total weight of the combined feed.

17. A method of claim 14, wherein the acetone concentration in the combined feed stream is about 1 to about 8 wt % of the total weight of the combined feed.

18. A method for manufacturing a polycarbonate comprising:

reacting p,p-bisphenol with a carbonate precursor, wherein the p,p-bisphenol is manufactured by a process comprising:

introducing a combined feed stream comprising a feed stream and a recycle stream into a reactor system comprising at least one reactor containing a catalytic proportion of an acid catalyst and wherein the combined feed stream comprises a carbonyl compound and a stoichiometric excess of phenol;

removing from the reactor system a reactor effluent;

splitting the reactor effluent into a crystallization feed stream and an effluent recycle stream;

extracting from said crystallization feed stream a bisphenol adduct, remainder comprising a mother liquor stream;

dehydrating said mother liquor stream and said effluent recycle stream in a dehydrator wherein excess water and carbonyl compound are removed; and recycling the dehydrated mother liquor and the dehydrated effluent recycle stream back to the combined feed stream to effect the production of p,p-bisphenol.

19. The method of claim 18, wherein the p,p-bisphenol is interfacially reacted with the carbonate precursor.

20. The method of claim 19, wherein the carbonate precursor is a carbonyl halide.

21. The method of claim 20, wherein the carbonyl halide is phosgene.

22. The method for claim 18, wherein the polycarbonate has a number average molecular weight of about 3,000 to about 1,000,000 grams/mole.

23. A method for manufacturing a polycarbonate comprising:

reacting p,p-bisphenol with a carbonic acid diester, wherein the p,p-bisphenol is manufactured by a process comprising:

introducing a combined feed stream comprising a feed stream and a recycle stream into a reactor system comprising at least one reactor containing a catalytic proportion of an acid catalyst and wherein the combined feed stream comprises a carbonyl compound and a stoichiometric excess of phenol;

removing from the reactor system a reactor effluent;

splitting the reactor effluent into a crystallization feed stream and an effluent recycle stream;

extracting from said crystallization feed stream a bisphenol adduct, remainder comprising a mother liquor stream;

dehydrating said mother liquor stream and said effluent recycle stream in a dehydrator wherein excess water and carbonyl compound are removed; and recycling the dehydrated mother liquor and the dehydrated effluent recycle stream back to the combined feed stream to effect the production of p,p-bisphenol.

24. The method of claim 23, wherein reacting the p,p-bisphenol with the carbonic acid diester is conducted in a melt.

25. The method of claim 22, wherein the carbonic acid diester is diphenyl carbonate.

26. The method for claim 22, wherein the polycarbonate has a number average molecular weight of about 3,000 to about 1,000,000 grams/mole.

* * * * *